United States Patent
Bonnefous

(10) Patent No.: US 6,436,043 B2
(45) Date of Patent: Aug. 20, 2002

(54) ULTRASONIC IMAGE PROCESSING METHOD AND EXAMINATION SYSTEM FOR DISPLAYING AN ULTRASONIC COMPOSITE IMAGE SEQUENCE OF AN ARTERY

(75) Inventor: Odile Bonnefous, Nogent-sur-Marne (FR)

(73) Assignee: Koninklijke Phillips Electronics N.V., Eindhoven (NL)

( * ) Notice: Subject to any disclaimer, the term of this patent is extended or adjusted under 35 U.S.C. 154(b) by 66 days.

(21) Appl. No.: 09/738,646

(22) Filed: Dec. 15, 2000

(30) Foreign Application Priority Data

Dec. 21, 1999 (EP) .............................. 99403229

(51) Int. Cl.[7] ................................................ A61B 8/00
(52) U.S. Cl. ...................................... 600/438; 600/450
(58) Field of Search ................................ 600/438, 437, 600/442–447, 453–456, 485, 500, 504, 450; 128/916

(56) References Cited

U.S. PATENT DOCUMENTS 4,660,564 A * 4/1987 Benthin et al. ............. 600/449
5,054,493 A * 10/1991 Cohn et al. ................. 600/485
5,090,411 A    2/1992 Higuchi .................. 128/660.05
5,107,840 A * 4/1992 Bonnefous ................... 600/454
5,316,004 A * 5/1994 Chesney et al. ............. 600/481
5,411,028 A * 5/1995 Bonnefous ................... 600/438
5,515,853 A * 5/1996 Smith et al. ................. 128/916
5,579,771 A   12/1996 Bonnefous ............. 128/661.04
5,830,131 A * 11/1998 Caro et al. .................. 600/300
6,113,543 A *  9/2000 Bonnefous ................... 600/438
6,246,898 B1 *  6/2001 Vesely et al. ................ 600/424

* cited by examiner

Primary Examiner—Marvin M. Lateef
Assistant Examiner—Ali M. Imam
(74) Attorney, Agent, or Firm—John Vodopia

(57) ABSTRACT

The invention concerns an ultrasonic signal processing method and system for constructing and displaying a composite image sequence wherein an image includes at least an ultrasonic grayscale 2-D image (A), representing a cross-section of an artery having a longitudinal axis (X) perpendicular to the grayscale image lines (Z), and a dilation curve image (B) of the artery along a grayscale image line coupled to the grayscale image (A). A movable pattern (AP) on the grayscale image (A) indicates a grayscale image line, so as to automatically generate the construction of the image (B) of the coupled dilation curve ($\Delta(X,n)$).

10 Claims, 4 Drawing Sheets

ULTRASONIC IMAGE PROCESSING METHOD AND EXAMINATION SYSTEM FOR DISPLAYING AN ULTRASONIC COMPOSITE IMAGE SEQUENCE OF AN ARTERY

The invention relates to an ultrasonic image processing method for displaying an ultrasonic examination image sequence of an artery segment with indications of the arterial dilation in function of the cardiac cycle. The invention also relates to an ultrasonic examination imaging system for carrying out this method.

The invention is used in the field of ultrasonic diagnostic imaging, for providing cardio-vascular non-invasive diagnostic tools for studying anomalies of arteries and notably stenoses. A primary diagnostic criterion for a stenosis is an abrupt reduction of the diameter of a suspect artery segment observed in an artery image. A more elaborate criterion is the study of the artery diameter dilation in function of the instant of the cardiac cycle and in function of the location along the artery segment. Therefore, in order to early diagnosing stenosed arteries, the medical field has a need for non-invasive means for providing artery images together with clear quantified indications of the arterial dilation. As a matter of fact, it is important to use non-invasive means instead of invasive means because invasive means modifies the artery pressure, hence the actual arterial dilation.

An ultrasonic image processing method for calculating dilation curves related to an artery segment is already known from the U.S. Pat. No. 5,579,771 (Bonnefous, Dec. 3, 1996). This document describes a method for characterizing an artery segment by ultrasonic imaging, using an array of ultrasonic transducers that produces a sectional frame, which is formed by image lines of a number of successive parallel excitation lines extending perpendicularly to the artery axis. Said array is coupled to a transmitter/receiver circuit, which provides high frequency signals to a signal processing system. Said system determines the arterial walls radial velocity and displacement amplitude values and further determines an arterial dilation curve in function of location and time. Such a curve is constructed by points representing the arterial dilation value in the arterial radial direction Z, at a given location corresponding to an excitation lines along the longitudinal X-axis of the artery, in function of excitation instants t, during a cardiac cycle. So, FIG. 4C of this document shows, superposed, the different dilation curves related to all the excitation lines of an ultrasonic signal corresponding to the examined artery segment, said lines being at regularly spaced locations along the X-axis of the artery.

A problem is that these dilation curves are not readily exploitable by a cardiologist. In particular, it is difficult to actually connect a dilation curve to a given excitation line in the image provided by the set of high frequency signals related to the artery segment: that means that it is difficult to connect a dilation curve to a location in the artery segment. So, it is quite difficult to connect a dilation value and a time instant of the cardiac cycle to said location in the artery segment. Such a connection must however be established in order to perform a successful study and a precise diagnosis of the suspect zone of artery.

It is an aim of the invention to provide an ultrasonic image processing method to automatically establish such a connection.

This problem is solved by means of a method as claimed in Claim 1.

This method offers the advantage that the arterial wall behavior is made clearly visible together with the parameters that are useful to establish the diagnosis.

An ultrasonic diagnostic system having display means and means for carrying out the method is claimed in Claim 7. This system constitutes a tool for non-invasive diagnostic of arterial wall anomalies.

BRIEF DESCRIPTION OF THE FIGURES

Specific embodiments of the invention will be described in detail hereinafter with reference to the accompanying diagrammatic drawings; therein.

DESCRIPTION OF THE PREFERED EMBODIMENTS

Figure 1A:
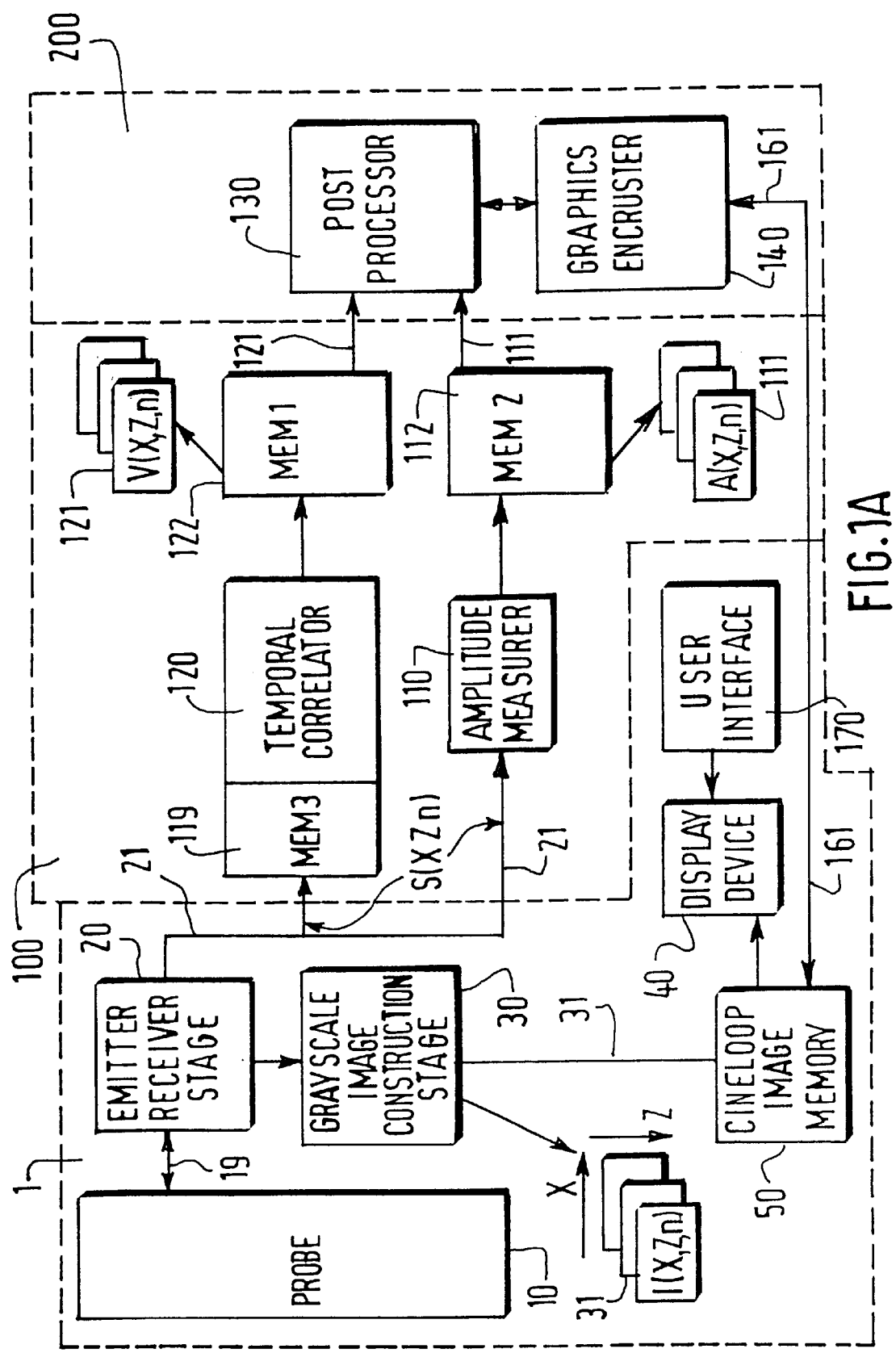
FIG. 1A shows a block diagram of an ultrasonic diagnostic imaging system for carrying out an image construction method and FIG. 1B shows a part of the first sub-system.

Referring to FIG. 1A, an ultrasonic diagnostic imaging system constructed in accordance to the principles of the present invention is shown in a block diagram form. In the example of embodiment that is described hereafter, this ultrasonic diagnostic imaging system is used as a tool for the examination of an artery 7 located in a medium 8. This ultrasonic diagnostic imaging system comprises sub-systems to perform an image processing method for the construction and display of a composite image sequence, which permits of visualizing an arterial segment whose walls have radial movements and of quantifying its radial arterial dilation, which occurs under the influence of the blood pressure, at given locations of said arterial segment and in-function of the different time instants during a cardiac cycle.

Figure 3:
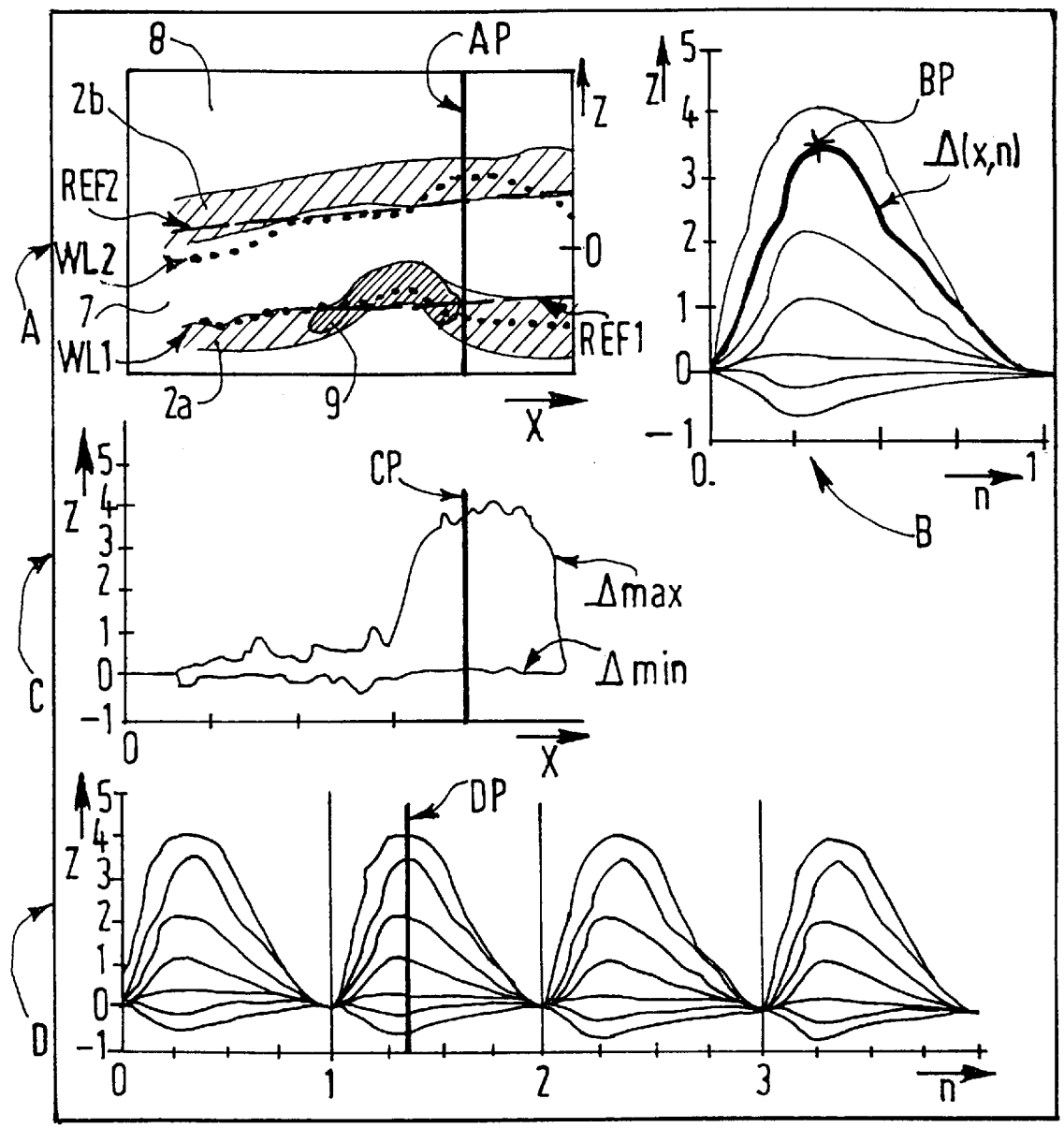
FIG. 3 shows an image constructed using the method.

1) Referring to FIG. 1A and FIG. 3, this image processing method comprises steps of acquiring ultrasonic signals related to the artery segment, said artery segment having a longitudinal axis denoted X-axis, and constructing and displaying a sequence of composite images, each image comprising at least:

a first display A of the grayscale image sequence representing said artery segment and a second display B of at least one specific curve of arterial dilation values along one specific direction of the Z-axis, said arterial dilation occurring under the influence of the blood pressure in function of time instants n of the cardiac cycle;

a pattern of a first cursor AP movable on the first display A, which cursor indicates a location X on the X-axis corresponding to a line of the grayscale image, and said specific arterial dilation curve of the second display B corresponding to said location X.

The ultrasonic diagnostic imaging system comprises interface means 170 to permit an user of positioning the movable cursor AP in display A to indicate one location X on the X-axis, and to automatically obtain the corresponding arterial dilation curve in display B.

2) Referring to FIG. 1 and to FIG. 3, this image processing method particularly comprises steps of constructing and displaying a composite image sequence, wherein:

a first display A of the grayscale image sequence representing said artery segment and a second display B of one whole set of curves of the arterial dilation values of the artery segment, along the radial direction of the Z-axis, in function of time instants n during the same cardiac cycle, each arterial dilation curve being related to a location X along the longitudinal X-axis of the arterial segment;

a pattern of a first cursor AP movable on the first display A, which cursor indicates a location X on the X-axis corresponding to a line of the grayscale image; a pattern of a second cursor BP movable on the second display B, which cursor indicates the specific arterial dilation curve corresponding to the location X and a time instant of the cardiac cycle;

and preferably a color-contrasting representation of the specific dilation curve in display B corresponding to said line of the grayscale image at location X;

said second cursor BP being coupled to the color-contrasting dilation curve and to the first cursor AP in order to provide the quantified value of the arterial dilation at the AP location X along the X-axis, and at a corresponding time instant n of the cardiac cycle.

The ultrasonic diagnostic imaging system comprises interface means to permit an user of positioning one of the movable cursors to indicate one parameter, for instance the first cursor AP to indicate the location X on the X-axis of the artery segment, and to automatically obtain the other parameters, that is the corresponding arterial dilation curve.

3) Preferably, this image processing method comprises steps of displaying a composite image sequence, wherein:

a first display A of the grayscale image sequence representing said artery segment; a second display B of one set of curves of the arterial dilation values of the artery segment, along radial directions parallel to the Z-axis, in function of time instants t of one given cardiac cycle; and a third display C of several successive sets of curves of the arterial dilation values of the artery segment, along radial directions parallel to the Z-axis, in function of the time instants t, corresponding to several successive cardiac cycles denoted CC1, CC2, CC3, . . . ;

a pattern of a first cursor AP movable on the first display A, which cursor indicates a location X on the X-axis corresponding to one line of the grayscale image; a pattern of a second cursor BP movable on the second display B, which cursor indicates the specific arterial dilation curve, preferably color-contrasting, corresponding to the location X on the X-axis of the first display A, and a time instant n of the cardiac cycle; a pattern of a third cursor CP movable on the third display C, which cursor indicates the specific set of arterial dilation curves corresponding to a given cardiac cycle, for instance the cardiac cycle denoted CC2 or any other, and a time instant n of said cardiac cycle;

said cursor CP being coupled to the second display B in order that the set of curves that are displayed in said second display B be the one indicated by said third cursor CP; and said third cursor CP being coupled to the second cursor BP in order that said second cursor BP indicates the same time instant as said third cursor CP; said second cursor BP being coupled to the first cursor AP in order to provide the quantified value of the arterial dilation at the location X along the X-axis of the artery segment, and the corresponding time instant n of the cardiac cycle.

The ultrasonic diagnostic imaging system comprises interface means 170 to permit an user of positioning two of the movable cursors to indicate two parameters in order to automatically obtain all other parameters. For instance, with the cursor CP indicating the cardiac cycle CC2, or any other, and the time instant n in said cardiac cycle in display C; and with the cursor AP indicating the location X along the X-axis of the artery segment, in order to automatically obtain:

the automatic reproduction in display B of said set of arterial dilation curves corresponding to the cardiac cycle selected by cursor CP in display C, for example CC2; the color-contrasting representation of the arterial dilation curve in display B that corresponds to the location X of cursor AP in display A; the time instant n and the dilation value at said location X given by cursor BP in display B and related to the location of cursor CP for the time instant and to cursor AP for the location X.

4) Preferably, this image processing method comprises steps of displaying a composite image sequence, wherein:

a first display A of the grayscale image sequence representing said artery segment; a second display B of one set of curves of the arterial dilation values of the artery segment, along radial directions parallel to the Z-axis, in function of the time instants n during one given cardiac cycle; a third display C of several successive sets of curves of the arterial dilation values of the arterial segment, along radial directions parallel to the Z-axis, in function of the time instants n, corresponding to several successive cardiac cycles denoted CC1, CC2, CC3, . . . ; a fourth display D of a first and second curves denoted Amax and Amin respectively, which are representations of the maximal and minimal dilation values in function of the time instants n in the selected cardiac cycle of display B;

a pattern of a first cursor AP movable on the first display A, which cursor indicates a location on the X-axis corresponding to a line of the grayscale image; a pattern of a second cursor BP movable on the second display B, which cursor indicates the specific arterial dilation curve, preferably color-contrasting, corresponding to the location on the X-axis of the first display A, and a time instant n of the cardiac cycle; a pattern of a third cursor CP movable on the third display C, which cursor indicates the specific set of arterial dilation curves corresponding to a given cardiac cycle, for instance the cardiac cycle denoted CC2, or any other, and a time instant n in said cardiac cycle; a pattern of a fourth cursor DP movable on the fourth display D, which cursor indicates a location X on the X-axis corresponding to a line of the grayscale image;

said third cursor CP being coupled to the second display B in order that the set of curves that is displayed in said second display B be the one indicated by said third cursor CP; and said third cursor CP being coupled to the second cursor BP in order that said second cursor BP indicates the same time instant n as said third cursor CP; said second cursor BP being coupled to the first cursor AP in order to provide the quantified value of the arterial dilation at the location X along the X-axis of the arterial segment, and the corresponding time instant of the cardiac cycle; and said fourth cursor DP following the first cursor AP and indicating the same location X.

This ultrasonic diagnostic imaging system comprises interface means to permit an user of positioning two of the movable cursors to indicate two parameters in order to automatically obtain all other parameters. For instance with the third cursor CP, indicating the cardiac cycle CC2, or any other, and the time instant n in said cardiac cycle in display C; and with the first cursor AP or the fourth cursor DP, indicating the location X along the Xaxis of the arterial segment, in order to automatically obtain:

the automatic reproduction in display B of said set of dilation curves corresponding to the cardiac cycle selected by the third cursor CP in display C for instance CC2; the color-contrasting representation of the arterial dilation curve in display B that corresponds to the location X of the first cursor AP in display A; the time instant n and the dilation value at said location X by the second cursor BP in display B; the maximal and minimal values of arterial dilation at location X during said cardiac cycle, for instance CC2.

5) Preferably, this image processing method further comprises steps of displaying a composite image sequence, wherein two graphic lines denoted WL1 and WL2, reproducing the movements of the lower and upper arterial walls, for enhancing the movements visibility during a given cardiac cycle, for instance CC2, are superposed unto the grayscale image of display A, occasionally together with two reference lines, REF1 and REF2, representing the mean wall positions at the instants of the cardiac cycle starts.

6) Preferably, the first, third and fourth patterns of cursors AP, CP and DP are lines of different colors, parallel to the lines of the images; the second pattern for cursor BP is a cross following the color-contrasting representation of the specific dilation curve.

FIG. 1A shows the ultrasonic diagnostic imaging system for the formation and display of the sequences of composite images as above-described, comprising the display of grayscale images with superposed graphics that diagrammatically represent the movements of the artery walls over one or several cardiac cycles and the displays of corresponding dilation curves. Cursors that are coupled between the different displays permits of quantifying the artery dilation with respect to the location along the artery longitudinal axis and to the cardiac cycle instant and of better detecting the anomalies of the wall movements. So, this ultrasonic diagnostic imaging system constitutes a tool for the diagnosis of lesions of arterial walls. This ultrasonic diagnostic imaging system comprises first, second and third sub-systems 1, 100, 200 respectively.

Referring to FIG. 1A, the operation of the sub-system 1 involves an ultrasonic probe 10 in contact with the medium 8 observed. The ultrasonic probe 10 transmits, via periodic excitations, ultrasonic signals to the medium scanned, in a direction OZ, and receives, in the same direction OZ, the echoes returned by the obstacles encountered in the medium. The probe is preferably composed of ultrasonic transducers which are assembled in a linear array parallel to the X-axis. A respective excitation line corresponds to each transducer.

Figure 1B:
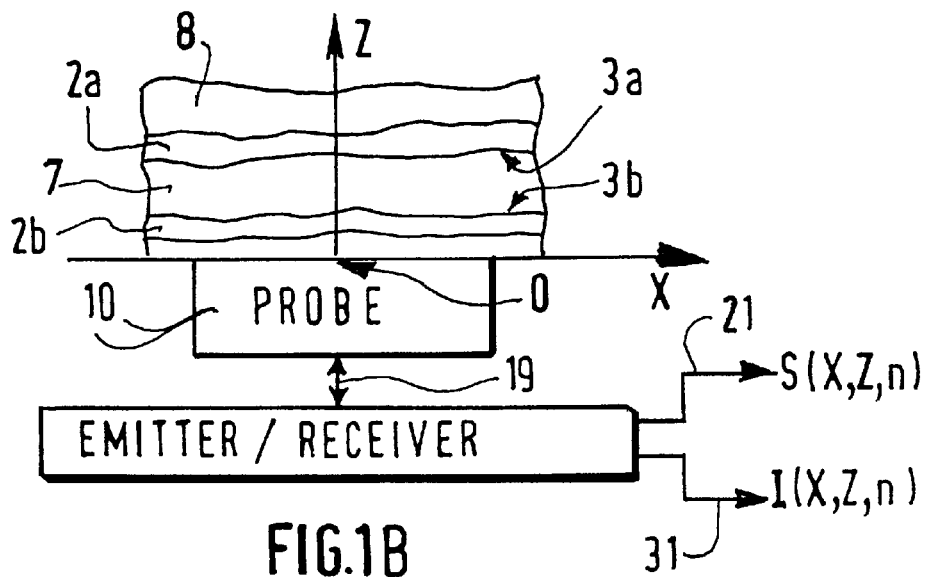

Referring to FIG. 1B, the examination of the medium by the ultrasonic probe 10 is performed in such a manner that the artery is scanned longitudinally in the direction parallel to OX in order to obtain longitudinal cross-sectional intensity images, enabling the visualization of the front wall 2a and the rear wall 2b. The direction of the transducer array is represented by the direction OX and the direction of the excitation lines is represented by the direction OZ. Therefore, the echographic image is scanned along the excitation lines of direction OZ which are the columns of the image. The probe is connected to an emitter/receiver stage 20. In a transmission step the medium is scanned along the directions of the excitation lines. In a receiving step, the image of each excitation line is formed, taking into account the propagation time in the medium and the amplitude of the echoes returned by the obstacles encountered along the excitation line considered. Preferably, in order to obtain a suitable resolution for the image, the ultrasonic excitations are focused during transmission as well as reception. The focusing and scanning operation in the emitter/receiver stage 20 provides acoustic high-frequency signals $S(X,Z,n)$ which enable the formation, as a function of the instant n, of a sequence of intensity images $I(X,Z,n)$ by way of an operation 30, n being the number of the image of the sequence. Each intensity image $I(X,Z,n)$ 21 is thus. formed by the scanning of each excitation line of the probe. The behavior of the artery is observed at least over a full cardiac cycle. Therefore, a sequence of a number N of images covering a time interval which is at least equal to a cardiac cycle is formed, N being a number 1<N. The number of image excitation lines may be, for example 68 with a scanning step (distance between excitation lines) of 0.5 mm; the number of image excitation lines may also be 112 with a scanning step of 0.25 mm. These characteristics enable visualization of an arterial segment of 28 mm. The delay between the signals corresponding to each excitation line of the image may be adjusted by increasing or decreasing the number of excitation lines and the distance between the excitation lines.

Referring to FIG. 1A, the intensity images $I(X,Z,n)$ 21 referred to as grayscale images are stored in an image memory 50 denoted Cineloop for further construction of the first display A. For the plotting of the graphic lines representing the movements of the arterial walls, which graphic lines are to be superposed unto the grayscale images, it is necessary to determine the velocity and the amplitude of the displacements of the walls.

Referring to FIG. 1A, the sub-system 100 includes a processor which executes the steps of processing the high-frequency signals $S(X,Z,n)$.

The sub-system 100 first performs a temporal correlation operation 120. The successive ultrasonic echoes are compared by way of their correlation function. The displacement of the biological structures from one ultrasonic emission to the next is estimated while taking into account the displacement of the correlation peak corresponding to the delay introduced by this displacement upon reception. For all objects scanned, the correlation operation 120 provides velocity measurements in the form of two-dimensional velocity images $V(X,Z,n)$ denoted 121. The correlation function is performed between the images of the image sequence so that it is necessary to have a rather large memory 119 denoted MEM3 available at the input of the module 120 performing the correlation operation. This memory 119 provides the necessary delay between two correlated signals.

Besides the velocity images 121 $V(X,Z,n)$, echo amplitude images 111 $A(X,Z,n)$ are also necessary to perform the further extraction and localization of the parietal velocities of the two-dimensional velocity images. They are used as segmentation means. These amplitude images 111 $A(X,Z,n)$ are obtained, in the sub-system 100, by means of an amplitude measurer 110. The memory 122 called MEM1 and the memory 112 called MEM2 store the results of the sub-system 100 that are respectively the velocity images $V(X,Z,n)$ and the echo amplitude images $A(X,Z,n)$.

Figure 2B:
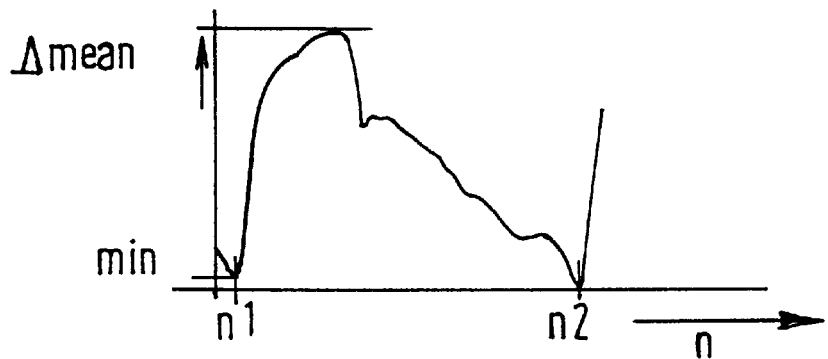
FIG. 2B shows a curve of mean dilation and FIG. 2C shows a set of dilation curves.
Figure 2C:
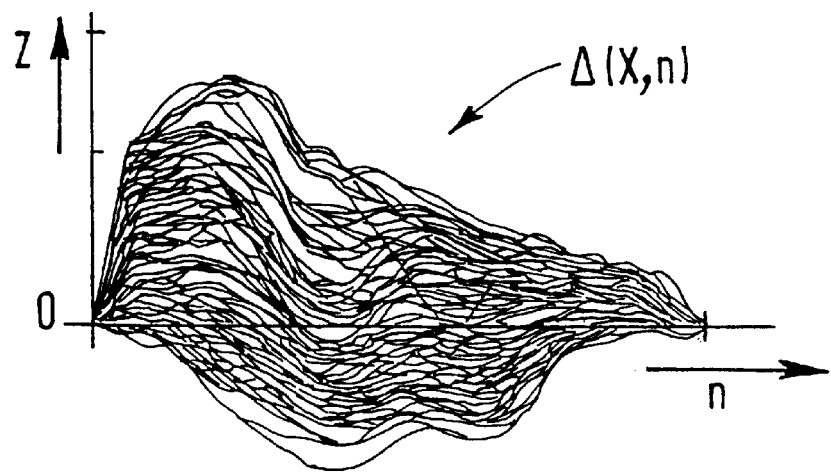
Figure 2A:
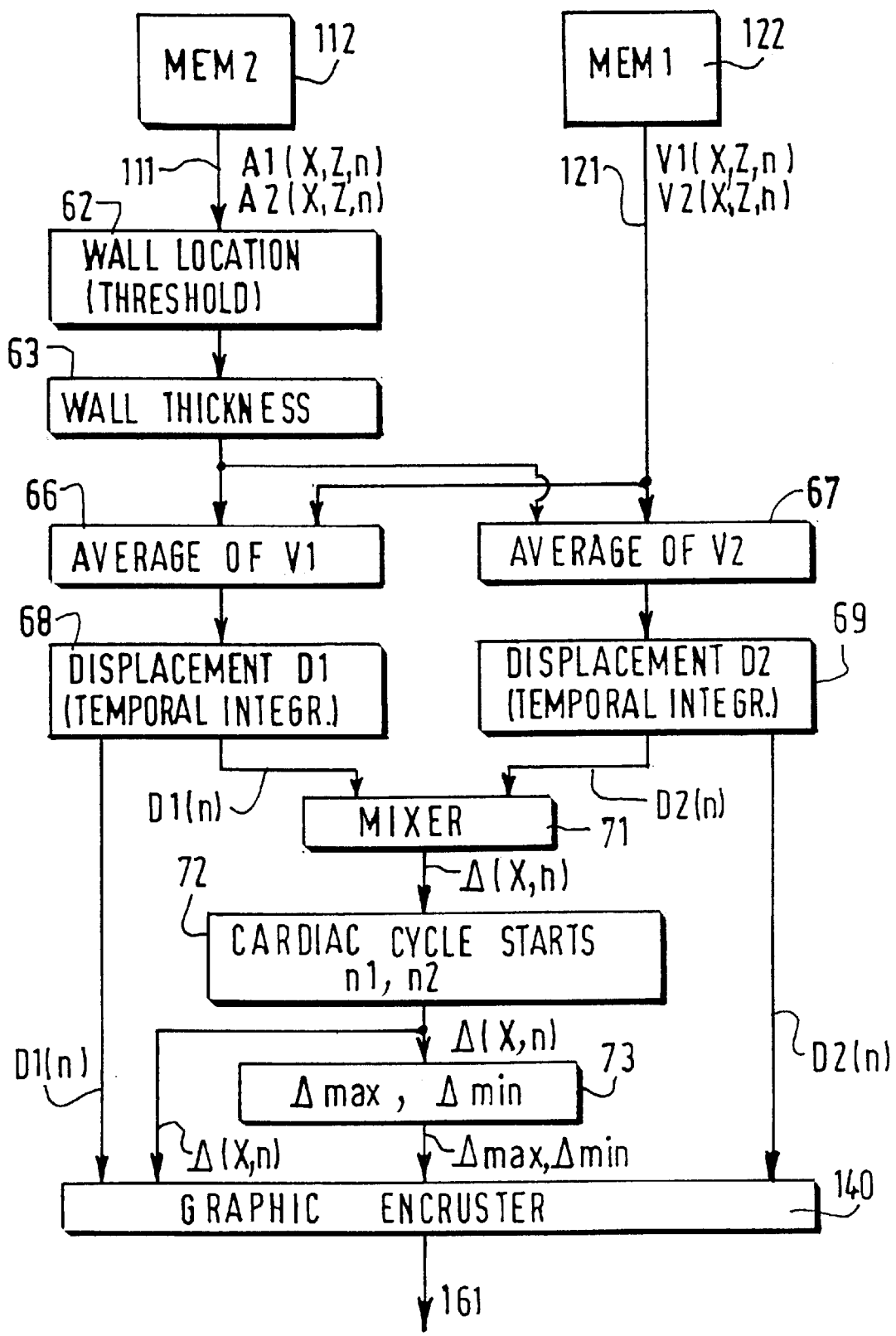
FIG. 2A shows a block diagram of the third sub-system.

Referring to FIG. 2A, the sub-system 200 comprises a processor, which executes the post-processing operation 130 applied to the results of the preceding operations 110 and 120 in order to determine the upper and lower wall displacements respectively $D1(X,n)$ and $D2(X,n)$, and the arterial radial dilation $\Delta(X,n)$. The principal steps of the operation 130 are:

application 62 of an adaptable threshold for each amplitude image 111 $A(X,Z,n)$ in order to perform the identification of the internal parietal boundary of the artery. This threshold produces digital images with black/white transitions between the interior and the exterior of the artery corresponding to the lower and upper internal parietal boundaries 3a, 3b. These transitions are filtered to eliminate discontinuities.

determination 63 of the respective thickness of each arterial walls. In the current implementation, a thickness value amounts to approximately 1 mm.

determination 66, 67 of an average value of the velocities through the thickness of the arterial wall, for example through the given thickness of 1 mm, determination 68, 69 of the displacements D1(X,n) and D2(X,n) between each image, by a temporal integration, for further construction of the display A;

determination of the arterial radial dilation Δ(X,n) calculated by a mixer 71 as the difference between the displacements D1(X,n) and D2(X,n) of the two walls, for the further construction of the displays B and C;

determination 72 of the starting points of the cardiac cycle by analysis of the temporal variations of the mean arterial dilation along the arterial X-axis ; a curve Δ(n) of the mean dilation is shown in FIG. 2B. The instants n1 and n2 corresponding to the minimum values MIN of mean dilation are identified as starts of cardiac cycles;

determination 73 of the curves Δmin and Δmax of the minimal and maximal values of the arterial dilation for the further construction of the display D.

Referring to FIG. 1A, after corrections taking into account the starting instants of the cardiac cycles, where the artery is non-dilated, i.e. has zero parietal displacements, the parietal displacements D1(X,n) and D2(X,n), the dilation curves Δ(X,n) and the curves Δmin and Δmax can be represented in relation to said starting points of the cardiac cycles for constructing the displays A, B, C and D and the patterns of the cursors AP, BP, CP, DP. These displays and cursor patterns are arranged and coupled by the encruster 140.

For constructing the display A of FIG. 3, the operation of the encruster 140 performs the graphic superposition of curves WL1 and WL2 corresponding to the parietal displacements D1(X,n) and D2(X,n) at the instant n on the grayscale images I(X,Z,n) which are stored in the memory 50 Cineloop. Reference lines REF1 and REF2 derived from the parietal boundary transitions extracted from the amplitude images, corresponding to the start of the cardiac cycle of the image sequence, are also preferably superposed.

For further constructing the composite image sequence of FIG. 3 already including the display A, the encruster 140 arranges the images of the display D with the extremities of the artery segment in visual correspondence with those in display A, for example as shown in FIG. 3. Patterns of cursors AP and DP are respectively superposed on said displays A and D and coupled so as to move correspondingly along the X-axis to give the measure of X.

For constructing the composite image sequence of FIG. 3 already including the displays A and D, the encruster 140 arranges the images of several arterial dilation curves in order to construct the display C on the same image screen and arranges a pattern of the cursor CP moving along the axis of time denoted n, apt to indicate a specific cardiac cycle.

For constructing the composite image sequence of FIG. 3 already including the displays A, D and C, the encruster 140 arranges the images of the specific arterial dilation curve corresponding to the selected cardiac cycle in display C in order to construct the display B coupled to the cursor CP on said same image screen; and arranges a pattern of the cursor BP moving along the axis of time denoted n and coupled to the cursors AP and DP in order to indicate a specific dilation curve corresponding to the location X on the X-axis of displays A and D.

For each operation, the graphics encruster module 140 fetches the image sequence in Cineloop and further stores it again afterwards by connection 161.

Referring to FIG. 1A, the ultrasonic processing system also comprises an interface 170 for the user to position or control the cursors AP, BP, CP, DP on the displays A, B, C, D on the screen of the display system 40. The display system, the processors and the memories may respectively be the screen 40, the processor 130 and the memory of a workstation as known of those skilled in the art. The workstation may also comprise a keyboard and a mouse used as an interface for the user to position or control the cursors AP, BP, CP, DP on the displays A, B, C, D on the screen. Preferably a color display system is used to display the color-contrasting dilation curve and cursors of different colors.

The invention can be applied to the processing of signals different from ultrasonic signals, for example electric, electromagnetic signals, etc.

During the display of the sequence on the display device 40, the physician can qualitatively and quantitatively evaluate the distortions or non-distortions of the graphic lines simulating and enhancing the displacements of the walls and derive therefrom the presence and the seriousness of stenosis, or elasticity defects, linked to the arterial walls of the subjacent grayscale image. The physician can also qualitatively and quantitatively evaluate the arterial dilation in real time, which enables optimization of the diagnosis.

What is claimed is:

1. Ultrasonic image processing method comprising steps of:

acquiring ultrasonic signals related to an object in a medium, said object having moving parts submitted to periodic dilation related to a substantially regular time cycle, constructing an ultrasonic grayscale 2-D image sequence (A) representing a cross-section of a segment of said object having a longitudinal axis (X) perpendicular to the grayscale image lines (Z), constructing a dilation curve image (B), related to the dilation of said moving parts along a grayscale image line, in function of time instants (n) of a time cycle, and coupling the dilation curve to the grayscale image line, and constructing a first movable pattern (AP) on the grayscale image (A), denoted first image, to indicate a grayscale image line, so as to automatically generate the construction of an image (B) of a coupled dilation curve (Δ(X,n)), denoted second image, and displaying a composite image sequence wherein an image includes a grayscale image (A) with the first movable pattern (AP) indicating a grayscale image line location (X) and the dilation curve of the second image (B) related to said first pattern location (X).

2. A method as claimed in claim 1, comprising further steps of:

constructing an image (B) of a set of dilation curves, denoted second image, related to the dilation of said moving parts along respectively each of the grayscale image lines, during a time cycle, and coupling each dilation curve to the related grayscale image line, and constructing a second movable pattern (BP) on the second image (B) of the set of dilation curves that is coupled to the first movable pattern (AP), which second pattern (BP) automatically indicates the dilation value at the image line location (X) of the first pattern (AP) and the time instant (n) of the time cycle, displaying a composite image sequence wherein an image includes a first grayscale image (A) with the first movable pattern (AP) and a second image (B) of the set of dilation curves ($\Delta(X,n)$), for the same time cycle, with the coupled second movable pattern (BP).

3. A method as claimed in claim 2, comprising further steps of:

constructing a third image (C) of several sets of dilation curves, related to the dilation of said moving parts along respectively each of the grayscale image lines and corresponding to several successive time cycles, and coupling each dilation curve to the related grayscale image line, and constructing a third movable pattern (CP) on the third image (C) of the several sets of dilation curves for indicating a specific set of dilation curves, a time instant during the time cycle corresponding to said set, said third movable pattern (CP) being coupled to the second movable pattern (BP), which automatically gives the dilation value at the image line location (X) indicated by the first pattern (AP) and the time instant (n) of the time cycle indicated by the third pattern (CP), displaying a composite image sequence wherein an image includes the first grayscale image (A) sequence with the first movable pattern (AP), the third image (C) of the several sets of dilation curves ($\Delta(X,n)$) with the third pattern (CP) and the second image (B) of the specific set of dilation curves indicated by the third cursor (CP), with the second pattern (BP), which gives the dilation value at the image line location (X) indicated by the first pattern (AP) and the time instant (n) of the time cycle.

4. A method as claimed in claim 3, comprising further steps of:

constructing graphic lines (WL1, WL2) representing the movements of the object moving parts and superposing said graphic lines, for enhancing the movements visibility in function of the time cycle, unto the first grayscale image sequence (A).

5. A method as claimed in claim 4, comprising further steps of:

constructing a fourth image (D) of a first curve and a second curve respectively of the minimal and maximal dilations during a time cycle, coupled to the first image sequence, and constructing a fourth movable pattern (DP) on the fourth image (D) coupled to the first pattern, displaying a composite image sequence wherein an image further includes the fourth image (D) and the fourth pattern (DP).

6. A method as claimed in claim 1 wherein the object is an artery, the moving parts are the artery walls moving under the blood pressure, the time cycles are the cardiac cycles, the grayscale image longitudinal axis is the artery axis, the dilation is the radial arterial dilation.

7. An ultrasonic examination imaging system to carry out the method according claim 7, comprising an ultrasonic probe coupled to an ultrasonic system for emitting and receiving ultrasonic signals from a medium with an object having moving parts, and comprising ultrasonic sub-systems to process the received ultrasonic signals with processors to construct the images and the corresponding patterns and graphics, memories to store the images, patterns and graphics, a display system to display the composite image formed by following the steps of said method and an interface for an user to move the movable patterns so as to automatically obtain the quantified parameters related to said moving parts.

8. A system as claimed in claim 7, having color display means to display color-contrasting curves and patterns having different colors.

9. A system as claimed in claim 7, comprising a suitably programmed computer of a workstation or a special purpose processor having circuit means, which are arranged to process ultrasonic signals according to the method, having means to display the images constructed according to said method processed according to said method, and having an user interface such as a mouse or a keyboard to permit the user of moving the movable patterns on the respective images of the composite image in order to automatically obtain the quantified parameters related to said moving parts.

10. A computer program product comprising the set of instructions for carrying out a method as claimed in claim 1.

* * * * *